(12) United States Patent
Witt

(10) Patent No.: US 8,716,025 B2
(45) Date of Patent: May 6, 2014

(54) DRIFTING TWO-DIMENSIONAL SEPARATION WITH ADAPTION OF SECOND DIMENSION GRADIENT TO ACTUAL FIRST DIMENSION CONDITION

(75) Inventor: Klaus Witt, Keltern (DE)

(73) Assignee: Agilent Technologies, Inc., Santa Clara, CA (US)

( * ) Notice: Subject to any disclaimer, the term of this patent is extended or adjusted under 35 U.S.C. 154(b) by 319 days.

(21) Appl. No.: 13/179,138

(22) Filed: Jul. 8, 2011

(65) Prior Publication Data

US 2013/0008859 A1  Jan. 10, 2013

(51) Int. Cl.
*B01D 15/10* (2006.01)
*B01D 57/02* (2006.01)
*B01D 17/12* (2006.01)
*G01N 35/00* (2006.01)

(52) U.S. Cl.
USPC ............ 436/50; 73/61.55; 204/451; 204/457; 204/602; 204/607; 210/138; 210/141; 210/198.2; 210/656; 210/739; 422/70; 422/105; 422/116; 422/527; 436/161; 436/177; 700/273

(58) Field of Classification Search
USPC .............. 73/61.55, 61.56; 210/138, 141, 143, 210/198.2, 259, 635, 656, 767, 806, 739; 204/600, 450, 451, 457, 602, 607; 422/70, 105, 116, 509, 527; 436/161, 436/43, 50, 177; 700/266, 273
See application file for complete search history.

(56) References Cited

U.S. PATENT DOCUMENTS

| | | | |
|---|---|---|---|
| 4,469,601 A * | 9/1984 | Beaver et al. ................. | 210/658 |
| 5,196,039 A * | 3/1993 | Phillips et al. ................ | 210/656 |
| 6,260,407 B1 * | 7/2001 | Petro et al. .................... | 73/61.52 |
| 6,416,663 B1 * | 7/2002 | Miroslav et al. ........... | 210/198.2 |
| 6,475,391 B2 * | 11/2002 | Safir et al. ....................... | 506/12 |
| 2003/0070988 A1 * | 4/2003 | Petro et al. .................... | 210/656 |
| 2003/0080062 A1 * | 5/2003 | Petro et al. .................... | 210/656 |
| 2003/0089663 A1 * | 5/2003 | Petro et al. .................... | 210/656 |
| 2004/0025575 A1 * | 2/2004 | Petro et al. .................. | 73/61.55 |
| 2007/0187243 A1 * | 8/2007 | Patton et al. .................. | 204/450 |
| 2009/0126466 A1 * | 5/2009 | Gilar et al. .................. | 73/61.55 |
| 2010/0073548 A1 * | 3/2010 | Meurrens ...................... | 348/345 |
| 2010/0116659 A1 * | 5/2010 | Liu et al. ....................... | 204/452 |
| 2010/0125863 A1 * | 5/2010 | Inoue ............................ | 720/704 |

OTHER PUBLICATIONS

Jandera et al, "Optimization of separation in two-dimensional high-performance liquid chromatography by adjusting phase system selectivity and using programmed elution techniques", Journal of Chromatography, vol. 1189, Published 2008, pp. 207-220.*

(Continued)

*Primary Examiner* — Joseph Drodge

(57) ABSTRACT

A control device for a sample separation apparatus, the sample separation apparatus including a first separation unit and a second separation unit downstream of the first separation unit and supplied with the fluidic sample after treatment by the first separation unit. A control device is configured for controlling the first separation unit to execute a primary separation sequence within a time interval for separating the fluidic sample into fractions, and for controlling the second separation unit to execute secondary separation sequences within the time interval for further separating the separated fractions into sub-fractions, wherein the secondary separation sequences form part of a common sample separation method defined by a common specification of the sample separation involving a set of parameters, and adjusting, over a progress of the primary separation sequence, at least one parameter according to which at least one of the plurality of secondary separation sequences is executed.

20 Claims, 6 Drawing Sheets

(56) References Cited

OTHER PUBLICATIONS

Stoll et al, "Fast comprehensive two-dimensional liquid chromotograpy", Journal of Chromotography, vol. 1168, Published Oct. 19, 2007.*

Pavel Jandera, Tomas Hajek, Petr Cesla, "Comparison of various second-dimension gradient types in comprehensive two-dimensional liquid chromatography", J. Sep. Sci. 2010, 33, 1382-1397.

* cited by examiner

DRIFTING TWO-DIMENSIONAL SEPARATION WITH ADAPTION OF SECOND DIMENSION GRADIENT TO ACTUAL FIRST DIMENSION CONDITION

The present invention relates to a sample separation system.

BACKGROUND

In liquid chromatography, a fluidic sample and an eluent (liquid mobile phase) may be pumped through conduits and a column in which separation of sample components takes place. The column may comprise a material which is capable of separating different components of the fluidic analyte. Such a packing material, so-called beads which may comprise silica gel, may be filled into a column tube which may be connected to other elements (like a control unit, containers including sample and/or buffers) by conduits. The composition of the mobile phase can be adjusted by composing the mobile phase from different fluidic components with variable contributions.

Two-dimensional separation of a fluidic sample denotes a separation technique in which a first separation procedure in a first separation unit is performed to separate a fluidic sample into a plurality of fractions, and in which a subsequent second separation procedure in a second separation unit is performed to further separate the plurality of fractions into sub-fractions. Two-dimensional liquid chromatography (2D LC) may combine two liquid chromatography separation techniques.

Pavel Jandera, Tomas Hajek, Petr Cesla, "Comparison of various second-dimension gradient types in comprehensive two-dimensional liquid chromatography", *J. Sep. Sci.* 2010, 33, 1382-1397, discloses that gradient elution provides significant improvement in peak capacity with respect to isocratic conditions. In the second dimension, gradients are limited to a short-time period available for separation. Various types of second-dimension gradients in comprehensive LC LC are compared: (i) "full in fraction", (ii) "segment in fraction" and (iii) "continuously shifting" gradients, applied in orthogonal LC LC separations of phenolic acids and flavones on a polyethylene glycol column in the first dimension and two types of porous shell fused-core C18 columns in the second dimension (Ascentis Express and Kinetex). The porous shell columns provide narrow bandwidths and fast second-dimension separations at moderate operating pressure that allows important savings of the overall separation time in comprehensive LC LC separations. The effects of the gradient type on the bandwidths, theoretical peak capacity, separation time and column pressure in the second dimension were investigated. The type of gradient program controls the range of lipophilicity of sample compounds that can be separated in the second-dimension reversed-phase time period. This range can be calibrated using alkylbenzene standards, to design the separation conditions for complete sample separation, avoiding harmful wrap around of non-eluted compounds to the subsequent second-dimension fractions.

However, such a concept of two-dimensional liquid chromatography is cumbersome for a user since the second dimension is divided into a plurality of completely unrelated gradient runs, involving the need for a user to program each of these gradient runs individually.

Furthermore, when plotting the result of a 2D LC measurement in a two-dimensional coordinate system, it may happen that relatively large area regions may remain empty or basically empty. This corresponds to the fact that a certain portion of the measurement time is spent inefficiently.

SUMMARY

It is an object of the invention to provide an efficiently operating two-dimensional sample separation apparatus. The object is solved by the independent claims. Further embodiments are shown by the dependent claims.

According to an exemplary embodiment of the present invention, a control device for a sample separation apparatus for separating a fluidic sample is provided, the sample separation apparatus comprising a first separation unit supplyable with the fluidic sample to be separated and a second separation unit downstream of the first separation unit and supplyable with the fluidic sample after treatment by the first separation unit, wherein the control device is configured for controlling the first separation unit to execute a primary separation sequence within a measurement time interval for separating the fluidic sample into a plurality of fractions, controlling the second separation unit to execute a plurality of secondary separation sequences within the measurement time interval for further separating at least a part of the separated plurality of fractions into a plurality of sub-fractions, wherein the secondary separation sequences form part of a common sample separation method defined by a common specification of the sample separation involving a set of parameters, and adjusting, over a progress of the primary separation sequence, at least one parameter according to which at least one of the plurality of secondary separation sequences is executed.

According to another exemplary embodiment of the present invention, a sample separation apparatus for separating a fluidic sample is provided, wherein the sample separation apparatus comprises a first separation unit supplyable with the fluidic sample to be separated, a second separation unit downstream of the first separation unit and supplyable with the fluidic sample after treatment by the first separation unit, and a control device having the above mentioned features for controlling operation of the first separation unit and the second separation unit.

According to still another exemplary embodiment of the present invention, a process of separating a fluidic sample by a first separation unit supplyable with the fluidic sample to be separated and by a second separation unit downstream of the first separation unit and supplyable with the fluidic sample after treatment by the first separation unit is provided, wherein the process comprises controlling the first separation unit to execute a primary separation sequence within a measurement time interval for separating the fluidic sample into a plurality of fractions, controlling the second separation unit to execute a plurality of secondary separation sequences within the measurement time interval for further separating at least a part of the separated plurality of fractions into a plurality of sub-fractions, wherein the secondary separation sequences form part of a common sample separation method defined by a common specification of the sample separation involving a set of parameters, and adjusting, over a progress of the primary separation sequence, at least one parameter according to which at least one of the plurality of secondary separation sequences is executed.

According to still another exemplary embodiment of the present invention, a software program or product is provided, preferably stored on a data carrier, for controlling or executing the process having the above mentioned features, when run on a data processing system such as a computer.

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied in the context of measurement control and measurement data analysis. The measurement control and measurement data analysis scheme according to an embodiment of the invention can be performed or assisted by a computer program, i.e. by software, or by using one or more special electronic optimization circuits, i.e. in hardware, or in hybrid form, i.e. by means of software components and hardware components.

In the context of this application, the term "fluidic sample" may particularly denote any liquid and/or gaseous medium, optionally including also solid particles, which is to be analyzed. Such a fluidic sample may comprise a plurality of fractions of molecules or particles which shall be separated, for instance biomolecules such as proteins. Since separation of a fluidic sample into fractions involves a certain separation criterion (such as mass, size, volume, chemical properties, charge etc.) according to which a separation is carried out, each separated fraction may be further separated by another separation criterion (such as mass, size, volume, chemical properties, charge etc.), thereby splitting up or separating a separate fraction into a plurality of sub-fractions.

In the context of this application, the term "fraction" may particularly denote such a group of molecules or particles of a fluidic sample which have a certain property (such as mass, volume, chemical properties, etc.) in common according to which the separation has been carried out. However, molecules or particles relating to one fraction can still have some degree of heterogeneity, sometimes simply because resolution of first separation process is not sufficient enough, but i.e. can be further separated in accordance with another separation criterion.

In the context of this application, the term "sub-fractions" may particularly denote individual groups of molecules or particles all relating to a certain fraction which still differ from one another regarding a certain property (such as mass, volume, chemical properties, etc.). Hence, applying another separation criterion for the second separation as compared to the separation criterion for the first separation allows these groups to be further separated from one another by applying the other separation criterion, thereby obtaining the further separated sub-fractions.

In the context of this application, the term "downstream" may particularly denote that a fluidic member located downstream compared to another fluidic member will only be brought in interaction with a fluidic sample after interaction with the other fluidic member (hence being arranged upstream). Therefore, the terms "downstream" and "upstream" relate to a flowing direction of the fluidic sample. In terms of the sample separation apparatus, the second separation unit is located downstream of the first separation unit.

In the context of this application, the term "sample separation apparatus" may particularly denote any apparatus which is capable of separating different fractions of a fluidic sample by applying a certain separation technique. Particularly, two separation units may be provided in such a sample separation apparatus when being configured for a two-dimensional separation. This means that the sample is first separated in accordance with a first separation criterion, and is subsequently separated in accordance with a second, different, separation criterion or a different selectivity of the same criterion (see RP-RP separations with different temperature on the two columns).

The term "separation unit" may particularly denote a fluidic member through which a fluidic sample is transferred and which is configured so that, upon conducting the fluidic sample through the separation unit, the fluidic sample will be separated into different groups of molecules or particles (called fractions or sub-fractions, respectively). An example for a separation unit is a liquid chromatography column which is capable of trapping and selectively releasing different fractions of the fluidic sample.

In the context of this application, the term "primary separation sequence" may particularly denote a separation method or a part thereof according to which a fluidic sample is to be separated in the first separation unit. This may include a plurality of steps to be carried out subsequently. The execution of these steps occurs over a so-called measurement time interval. In a preferred embodiment, the primary separation sequence is a gradient run by which the fluidic sample is separated in the first separation unit by changing a ratio of two (or more) solvents gradually, thereby selectively trapping and later releasing individual fractions of the fluidic sample on the first separation unit.

In the context of this application, the term "plurality of second separation sequences" may particularly denote sequences having a similar or the same characteristic as the first sequence but which are to be executed by the second separation unit. Furthermore, each of the second separation sequences is executed over a time interval being smaller than the measurement time interval relating to the primary separation sequence. In other words, several or many secondary separation sequences may be carried out within a time interval of the primary separation sequence. This means that the fluidic sample is split or separated into the various fractions during execution of the primary separation sequence, whereas the secondary separation sequences chop the separated fractions into further subsections by applying another, at least partially different separation criterion. For instance, a number of secondary separation sequences relating to one primary separation sequence may be in a range between 5 and 3000, particularly between 10 and 500.

In the context of this application, the term "(primary) measurement interval" may particularly denote a time interval required for executing the primary separation sequence. Such a time interval may be in a range between 1 min and 5 h, particularly between 5 min and 1 h. It may relate to the time required for executing a gradient run on a first separation unit configured as a liquid chromatography column. In accordance with the long-lasting primary separation sequence, the sample can be separated into a plurality of fractions by a first separation criteria (for instance the size). In the subsequent, at least partially orthogonal secondary separation sequences, each fraction separated during the primary separation sequence can be further separated into a plurality of sub-fractions (particularly in accordance with another separating criterion like chemical property such as solubility).

In the context of this application, the term "progress of the primary separation sequence" means the time period between a start and the actual measurement time interval. In parallel there are several second separation sequences performed, which hold a parameter that depends on progress of the primary separation. Therefore, during execution of the primary separation sequence, an adjustment of the parameters of the secondary separation sequences, may be performed. This may require or simply include that the progress (or clock) of the primary separation unit is communicated to the second separation unit, or vice versa.

In the context of this application, the term "parameter according to which one of the plurality of separation sequences is executed" may particularly denote one or more quantitative values (such as a value of a solvent composition, a temperature, the duration of a secondary separation sequence) and/or one or more qualitative measurement parameters (such as an operation mode according to which a separation unit is operated) which can be changed under control of the control unit and/or based on user input over the duration of the measurement time interval.

In the context of this application, the term "common sample separation method defined by a common specification of the sample separation involving a set of parameters" may particularly denote a workflow, an algorithm or a set of operation parameters defining as to how a sample separation apparatus is to be operated or run. Thus, the common sample separation method may include a complete set of data which, when provided to the sample separation apparatus, defines a dedicated operation of this sample separation apparatus. For example, the common sample separation method may define a procedure of separating different components of fluids by the sample separation apparatus (for example a recipe as to how to run a liquid chromatography, gas chromatography or gel electrophoresis experiment) or a procedure requiring official approval (for instance an approval procedure before the FDA, Food and Drug Administration, in the United States), a procedure of flushing the device (for example an algorithm according to which a rinse solution is supplied for removing traces of fluids from a previous investigation, thereby suppressing undesired crosstalk or contamination), a selection of a solvent for the sample separation apparatus (for instance selecting multiple constituents of such a solvent, their relative concentrations, etc.), a procedure of applying a concentration gradient to the sample separation apparatus (for example to perform a liquid chromatography analysis using a chromatographic column) and/or a selection of an operation temperature (and/or other physical parameters such as pressure) for the sample separation apparatus. The operation mode may define a sequence of instructions providable to the sample separation apparatus for operating the sample separation apparatus. Such a set of instructions may be sufficient for running the fluidic device in accordance with a desired scheme. Particularly in the field of two-dimensional liquid chromatography, the sample separation may be a chromatographic method.

According to an exemplary embodiment of the invention, a two-dimensional separation of a fluidic sample, i.e. a separation of a fluidic sample based on two different separation criteria, is carried out in a parameterizable manner, what concerns the separation in the second dimension. Normally a gradient is programmed as a timetable (TTBL) in which at specific time points fixed values are commanded, but now in a simple approach e.g. in this TTBL so-called 'key'-values are entered, for which at the given execution time the progress of the first dimension separation is monitored, from which these key-values are filled in. The progression or gradient of these key-values may be given in a TTBL. This gives a user-friendly and intuitive way of defining such progressive execution protocol. In other words, not a strict execution of certain primary and secondary separation sequences is required, but in contrast to this the second dimension of such a two-dimensional separation system is adjusted, for instance continuously, by manipulating a parameter set. For example, the result of a corresponding two-dimensional separation result is plottable along a two-dimensional coordinate system, plotting a first separation criterion (such as a retention time of a first liquid chromatography separation) along one axis and plotting a second separation criterion (for instance a retention time according to a second, different liquid chromatography separation) along the second axis. An equal distribution of the individual peaks relating to individual fractions and sub-fractions over this two-dimensional area assumes that two separation criteria are completely orthogonal, i.e. that there is no correlation between them. This is however not always true in reality. For instance, one may think about a first separation criterion based on mass and a second separation criterion based on volume of the particles. It is quite unlikely that the particles with an extraordinarily high mass have at the same time an extraordinarily small volume. In view of such partial deviations from complete orthogonality between the two separation criteria, the arrangement of the peaks over the two-dimensional plotting area is not homogeneous, thereby not using efficiently the two-dimensional plot. Furthermore, value of the measurement time is lost in specific regions of a two-dimensional plot (relating to the measurement) in areas in which only few or no peaks of interest can be found. Exemplary embodiments of the invention now address this phenomenon and allow the parameters of the secondary separation sequence to be adjusted for more efficiently using resources in terms of measurement time, sample separation apparatus and display of results thereof. The hierarchical approach of defining the course of action of the secondary separation sequences in terms of the progress of the primary separation sequence has turned out to be capable of rendering the two-dimensional separation procedure more efficient and flexible for a user.

By configuring the sample separation system so that the secondary separation sequences form part of a common sample separation method defined by a common specification of the sample separation involving a set of parameters (for instance one data set stored in one file), it may be ensured that the separation method remains always the same, i.e. is not changed, over execution of the sample separation or during the measurement time interval. A skilled person will understand that a method change will require a significant amount of time (for example at least 10 seconds) so that changing a method for adjusting a parameter over a progress of the first separation sequence would involve significant delay and may even disturb the sample separation or may deteriorate separation performance. In contrast to this, an embodiment of the invention defines at least all secondary separation sequences in terms of a single common separation method simultaneously allowing for an adjustment of parameters of the secondary separation sequences over the progress of the first separation sequence.

Particularly, such an embodiment can be denoted as a tune-type parameter adjustment concept. While in the above example regarding the key values, the systems works more like a look-up-table, the concept of tune-type parameters has more of a self-perpetuating character. For instance, such a concept may define development of a parameter by a rule such as "start at 5, increment by 2% until 8 is reached". Also a complex mathematical function may be defined here which may even consider data or results from previous separation experiments or expert rules. It is for example possible to perform a scouting run, wherein a present peak distribution is used for improving or optimizing the use of a two-dimensional display area. It is possible to program shapes such as gradients in the second dimension by using placeholders which may assume different values over the progress, the running time or measurement time interval, of the first dimension. Thus, selective adaptation or adjustment of many secondary separation sequences can be enabled by only a very limited set of points of support (or sampling points), or even by a relation or function.

In the following, further exemplary embodiments of the control device will be explained. However, these embodiments also apply to the sample separation system, the process, and the software program or product.

In an embodiment, the common specification of the common sample separation method comprises a parameterized shape relation defined for at least two of the, particularly for all of the, secondary separation sequences in common, and a development instruction defining the parameters of the shape relation for the at least two, particularly for all, of the secondary separation sequences over a progress of the first separation sequence The term "parameterized shape relation" (or envelope) may particularly denote a relation between experimental variables (such as measurement time and solvent composition) defining a process flow for the group of the two or all secondary separation sequences. For instance in terms of a chromatographic gradient run, each secondary separation sequence may be defined by the general shape of a slow rising edge followed by a fast falling edge, possibly with constant sections in between. One or more parameters may individualize such a general shape relation differently for different second separation sequences. In other words, the general shape relation may be the same for the group of two or all secondary separation sequences, whereas its parameters may be different for different secondary separation sequences, thereby individualizing or adjusting them for an individual secondary separation sequence. In an embodiment, the shape relation may be a shape function. At least a part of the parameters of the shape relation may be at least part of the parameter or parameters which is or are adjusted over the progress of the primary separation sequence.

In an embodiment, the development instruction comprises a development relation defining development of the parameters, i.e. defining an abstract relation between parameter values and a number of a secondary separation sequence in a chronological order. The term "development relation" may particularly denote a (mathematic) relation, more particularly a (mathematic) function, defining development of the parameters for each secondary separation sequence in terms of a relation or a rule. For instance, the development relation may be a polynomial function or a trigonometric function. For adjusting development of a certain parameter over a number of, for instance fifty, secondary separation sequences, it may be sufficient for a user to simply define the development instruction in abstract terms without the need to manually type in a huge number of parameter values for each secondary separation sequence separately (as would be required if each of the secondary separation sequences would be configured as a separate separation method). This makes the task of adjusting parameters, or even re-adjusting parameters of existing methods, feasible for a user. In an embodiment, the development instruction may comprises a sample specific shape and progression calculated based on data from a previous analytical separation. Thus, knowledge from historical experiments may also be used as a basis for determining the development characteristic.

Additionally or alternatively, the development instruction comprises a set of specific parameter values, each being assigned to a specific secondary separation sequence in a chronological order, stored in a development database. A development database (such as a lookup table) may define the parameters for each secondary separation sequence in terms of specific parameter values. Thus, user guidance may be significantly improved by the concept of depositing the parameters in a machine-readable manner without the need for a user to manually input individual parameters for each of, for instance fifty, secondary separation sequences. Therefore the concept of development instructions may make the adaptation of the secondary separation sequence over the measurement time interval manageable.

In an embodiment, the primary separation sequence forms part of the same common sample separation method as the secondary separation sequences. Hence, the entire two-dimensional separation may be performed in terms of a single common separation method, i.e. one common set of instructions and parameters, rendering parameterization feasible and handling fast. For a liquid chromatography embodiment, this means that both the primary as well as the secondary separation sequences may be defined in terms of a common chromatographic method defining the two-dimensional liquid chromatography separation as a whole or in an integrated architecture.

In an embodiment, the control device is configured for adjusting the at least one parameter so that gradient runs, as the plurality of secondary separation sequences, perform a drift, particularly a continuous drift, while another gradient run is executed as the primary separation sequence. In such an embodiment, a number of gradient curves are carried out as the secondary separation sequences. Such a gradient (as an example for a shape function) may start at a base value (as an example for an adjustable parameter of the shape function), may continue with a certain solvent composition up to a final value (as an example for an adjustable parameter of the shape function) along a for instance linear curve, may stay constant for awhile (as an example for an adjustable parameter of the shape function) and may then go back down again to the initial base value of the solvent composition. In the described embodiment, a number of secondary separation sequences now may use correspondingly shaped time dependencies of the solvent composition which may however be shifted relative to one another along a vertical axis defining solvent composition. Therefore, in a plotting diagram, the focus of the measurement time may be set on plotting sections in which many or particularly interesting species are expected. This allows to more efficiently utilize resources in terms of measurement time, software and hardware.

In an embodiment, at least one of the primary separation sequence and the plurality of secondary separation sequences relate to a chromatographic gradient run. In such an embodiment, both separation units are chromatographic separation columns filled with beads for trapping and selectively releasing individual fractions of the fluidic sample. The two columns may differ, for instance with regard to their chemical interaction with the fluidic sample, particle size, porosity, temperature or any other separation-related property. However, in other embodiments, other kinds of separation techniques may be combined, for instance chromatography with electrophoresis, mass spectroscopy, etc.

In an embodiment, at least one of the plurality of secondary separation sequences is parameterized, wherein at least a part of corresponding parameters is adjusted over the progress of the primary separation sequence in accordance with a predefined progress rule. Such a progress rule may be an abstract rule (such as a relation, a function, an iterative rule, or a decision criterion) in accordance with which a value of the parameter develops with ongoing primary separation sequence progressing over time. Therefore, particularly the parameters indicating the individual secondary separation sequences can be adjusted. However, additionally or alternatively, also an adjustment of the primary separation sequence can be performed, under control of a user and/or of the control unit.

In an embodiment, at least two, particularly each, of the plurality of secondary separation sequences relate to a parameterized shape relation defined as a gradient curve starting from a first local extreme value (as a reference point, such as a local minimum or base value, or a local maximum or top value), subsequently rising or falling to a second local extreme value (as another reference point, such as a local maximum or top value, or a local minimum or base value) and then falling or rising to a next first local extreme value (local minimum or local maximum), wherein at least a part of corresponding parameters of the parameterized gradient curves is adjusted over the progress of the primary separation sequence. More specifically, at least two, particularly each, of the plurality of secondary separation sequences relates to a parameterized shape relation defined as a gradient curve starting from a base point, subsequently rising to a top point and then dropping to a next base point, wherein at least a part of corresponding parameters of the parameterized gradient curves is adjusted over the progress of the primary separation sequence. Hence, the above-mentioned shape relation may define a chromatographic gradient run in abstract terms. In such an embodiment, the parameters may be the solvent composition at the base point, the solvent composition of the top point, the slope of the gradient, the time interval for advancing from the bottom point to the top point, etc. For example, the solvent composition of the base point may be adjusted across the primary separation progress for every other secondary separation sequences in accordance with a continuously increasing function. In an alternative embodiment, it is also possible that at least two, particularly each, of the plurality of secondary separation sequences relates to a parameterized shape relation defined as a gradient curve starting from a top point, subsequently dropping to a base point and then rising to a next top point, wherein at least a part of corresponding parameters of the parameterized gradient curves is adjusted over the progress of the primary separation sequence. Such an embodiment may relate to a scenario in which the gradient runs in the opposite direction as compared to the previous embodiment, for example from 95% to 40% (for instance in the case of hydrophilic interaction liquid chromatography, HILIC). In a further alternative embodiment, the reference points of the secondary separation sequences need not be local extreme values (i.e. local minima or maxima), but can also relate to a position in the sequence at which a kink (i.e. a position at which the first derivative of the gradient curve is not continuous), etc. occurs in the gradient curve. Before and after such a kink, the algebraic sign of the first derivative of the gradient curve may be the same, wherein the algebraic sign of the first derivative of the gradient curve changes at a local extreme value.

In an embodiment, the control device is configured so that the first local extreme values (base points and/or the top points) are adjusted to differ among different ones of the plurality of secondary separation sequences, particularly to continuously increase (or alternatively continuously decrease) along a succession of the plurality of secondary separation sequences. In other words, the later a certain secondary separation sequence within the primary measurement interval, the higher the base point will be at which the secondary separation sequence starts for the next gradient run in the second dimension.

In an embodiment, the primary separation sequence relates to a parameterized shape relation defined as a gradient curve starting from a first local extreme value, subsequently rising or falling to a second local extreme value, and then falling or rising to the first local extreme value. More specifically, also the primary separation sequence relates to a parameterized gradient curve starting from a base point, subsequently rising to a top point, and then dropping to the base point, or vice versa. Hence, not only the secondary separation sequences may be parameterized, but also the first separation sequence may be defined by one or more parameters which can also be adjusted. Thereby, the flexibility of the system can be further increased.

In an embodiment, the control device comprises a determining unit configured for determining a two-dimensional plot representing the separation of the fluidic sample into the plurality of fractions along a first dimension and for representing the separation of the separated plurality of fractions into the plurality of sub-fractions along a second dimension. In such an embodiment, the two-dimensional plot may be displayed on a display device (such as a monitor) for allowing a user to visually perceive the result of the fluidic sample separation. The two dimensions or axes may be perpendicular so that the separation in accordance with the first separation unit and therefore first separation criterion may be plotted for instance along an abscissa, whereas the separation by a second separation unit may be plotted along an ordinate, or vice versa. Each fraction or sub-fraction may then be visible as a certain peak or spot in this two-dimensional coordinate system.

In an embodiment, the control device is configured for adjusting the at least one parameter in accordance with a rule or optimization algorithm to increase a degree of homogeneity according to which the sub-fractions are distributed over the two-dimensional area of the two-dimensional plot. The adjustment of the one or more parameters may therefore be performed so as to better use the available two-dimensional display area of the plots. By skipping or rapidly scanning over regions of the display area in which no peaks, no interesting peaks, or only a very small density of peaks is expected or predicted, measurement resources may be used more efficiently.

In an embodiment, the control device is configured for adjusting the at least one parameter so as to equally distribute the sub-fractions over the two-dimensional area of the two-dimensional plot. Such an equal distribution of peaks over a two-dimensional display area may sound manipulative on a first view. Therefore, in order to indicate to a user that a rescaling of the axis has been performed as a result of the adjustment of the parameters, a corresponding function according to which the representation along one of the two axes deviates from a linear representation may be indicated along the axis by markers or with a bar indicating such a density of display by a color code.

In an embodiment, the control device is configured for determining information indicative of at least one low-density region of peaks relating to the sub-fractions over the two-dimensional area of the two-dimensional plot, and is configured for adjusting the at least one parameter so that density of the peaks is increased in the at least one low-density region (may be decreased in at least one high-density region) of the two-dimensional plot as a result of the adjusting. By taking this measure, insufficiently used display area resources may be detected, and the separation sequence may be adjusted so as to more efficiently use such regions of displaying.

In an embodiment, the control device is configured for adjusting the at least one parameter in accordance with a user input. Therefore, it is also possible to perform the secondary separation sequences in accordance with user preferences or user selection, for instance in a scenario in which a user is only interested in information regarding a certain portion of the fractions or sub-fractions and is not interested in other fractions or sub-fractions. Then, the measurement may be focused on such interesting spots which may be then detected more accurately or more quickly. Furthermore, also the display characteristic of the individual peaks may be adjusted by a user by correspondingly adjusting parameters such as slope of a gradient curve, time spent for a secondary separation sequence, specific solvent compositions, etc.

In an embodiment, the control device is configured for adjusting a solvent composition during a chromatographic run as the at least one parameter. For example, such a solvent may be a mixture of water and acetonitrile (ACN). The solvent composition is then the ratio between two (or more of) such solvents, for instance a ratio between water and ACN. The characteristics according to which such a ratio and therefore the solvent composition changes over time may be parameterized and adjusted over the progress of the primary separation sequence.

In an embodiment, the control device is configured for adjusting a time to volume characteristic, particularly a flow rate, during a chromatographic run as the at least one parameter. For example, the time may denote the progress of the measurement time interval. The volume or volume-related parameter may be any fluid volume, for instance of a mobile phase and/or the fluidic sample. By adjusting the relation between time and volume, the flow rate may be adjusted.

In an embodiment, the control device is configured for adjusting a temperature of the first separation unit and/or the second separation unit as the at least one parameter. Hence, also external parameters such as temperature or even pressure can be adjusted for the separation units so as to modify the separation criteria applied by the two at least partially orthogonal separation procedures.

In the following, further exemplary embodiments of the sample separation system will be explained. However, these embodiments also apply to the control device, the process, and the software program or product.

In an embodiment, the first separation unit and the second separation unit are configured so as to execute the respective sample separation in accordance with different separation criteria, particularly in accordance with at least partially but not completely orthogonal separation criteria. In this context, the term "orthogonal" may particularly denote the conventional but not very accurate understanding that two different separation criteria in a two-dimensional liquid chromatography system are completely decoupled. This is not the case in practice, since for instance a separation with regard to mass and a separation with regard to volume of particles such as molecules are not completely independent. Exemplary embodiments of the invention make benefit of this cognition and propose to adjust the parameters under consideration of the fact that the separation criteria of the two separation units are not completely independent from one another. This has an impact on the regions in a two-dimensional chromatogram in which the likelihood to derive a high density of fractions is higher than in other regions. This can be addressed by the adjustment of the parameters.

In an embodiment, the first separation unit and the second separation unit are configured so as to execute the respective sample separation on identical separation media but with different operating conditions. Such operating conditions may be different solvents, different steepness of elution gradients, different column temperatures, different flows and/or different pressures, so that the separation criteria are partially but not completely orthogonal. However, not or not only the separation units may relate to non-completely orthogonal separation, but additionally or alternatively it is possible that the partial orthogonality is achieved by using a similar or even the same separation technique, but by adjusting the apparatus properties so that a partial orthogonality is obtained. For example, it is possible to use twice the same separation column, but to operate it at different temperature and/or with different solvents or solvent compositions.

In an embodiment, the first separation unit and the second separation unit are configured so as to execute the respective sample separation on identical separation media but with different operating conditions, particularly at least one of the group consisting of different solvents, different steepness of elution gradients, different column temperatures, different flows and different pressures, so that the separation criteria are partially but not completely orthogonal. However, not or not only the separation units may relate to non-completely orthogonal separation, but additionally or alternatively it is possible that the partial orthogonality is achieved by using a similar or even the same separation technique, but by adjusting the apparatus properties so that a partial orthogonality is obtained. For example, it is possible to use twice the same separation column, but to operate it at different temperature and/or with different solvents or solvent compositions.

In an embodiment, at least one of the first separation unit and the second separation unit is configured for performing a separation in accordance with one of the group consisting of liquid chromatography, supercritical-fluid chromatography, capillary electrochromatography, electrophoresis and gas chromatography. However, other separation techniques may be applied as well.

In an embodiment, the sample separation apparatus is configured as a two-dimensional liquid chromatography sample separation apparatus. It is possible to apply a so-called heart cutting approach. In such an operation mode, the second dimension (relating to the secondary separation sequences) is only carried out specifically and individually for specific regions, for instance since the separation along the first axis has shown that it might be worthwhile to further separate sub-fractions of a corresponding fraction. Each of the identified fractions might be separated by a different second dimension operating condition or sequence.

The first and/or second separation unit may be filled with a separating material. Such a separating material which may also be denoted as a stationary phase may be any material which allows an adjustable degree of interaction with a sample so as to be capable of separating different components of such a sample. The separating material may be a liquid chromatography column filling material or packing material comprising at least one of the group consisting of polystyrene, zeolite, polyvinylalcohol, polytetrafluorethylene, glass, polymeric powder, silicon dioxide, and silica gel, or any of above with chemically modified (coated, capped etc) surface. However, any packing material can be used which has material properties allowing an analyte passing through this material to be separated into different components, for instance due to different kinds of interactions or affinities between the packing material and fractions of the analyte.

At least a part of the first and/or second separation unit may be filled with a fluid separating material, wherein the fluid separating material may comprise beads having a size in the range of essentially 0.1 µm to essentially 50 µm. Thus, these beads may be small particles which may be filled inside the separation section of the microfluidic device. The beads may have pores having a size in the range of essentially 0.01 µm to essentially 0.2 µm. The fluidic sample may be passed through the pores, wherein an interaction may occur between the fluidic sample and the surface of the pores.

The sample separation apparatus may be configured as a fluid separation system for separating components of the sample. When a mobile phase including a fluidic sample passes through the fluidic device, for instance by applying a high pressure, the interaction between a filling of the column and the fluidic sample may allow for separating different components of the sample, as performed in a liquid chromatography device.

However, the sample separation apparatus may also be configured as a fluid purification system for purifying the fluidic sample. By spatially separating different fractions of the fluidic sample, a multi-component sample may be purified, for instance a protein solution. When a protein solution has been prepared in a biochemical lab, it may still comprise a plurality of components. If, for instance, only a single protein of this multi-component liquid is of interest, the sample may be forced to pass the columns. Due to the different interaction of the different protein fractions with the filling of the column (for instance using a gel electrophoresis device or a liquid chromatography device), the different samples may be distinguished, and one sample or band of material may be selectively isolated as a purified sample.

The sample separation apparatus may be implemented in different technical environments, like a sensor device, a test device, a device for chemical, biological and/or pharmaceutical analysis, a capillary electrophoresis device, a capillary electrochromatography device, a liquid chromatography device, a gas chromatography device, an electronic measurement device, or a mass spectroscopy device. Particularly, the fluidic device may be a High Performance Liquid device (HPLC) device by which different fractions of an analyte may be separated, examined and/or analyzed.

The sample separation unit element may be a chromatographic column for separating components of the fluidic sample. Therefore, exemplary embodiments may be particularly implemented in the context of a liquid chromatography apparatus.

The sample separation apparatus may be configured to conduct the mobile phase through the system with a high pressure, particularly of at least 600 bar, more particularly of at least 1200 bar.

The sample separation apparatus may be configured as a microfluidic device. The term "microfluidic device" may particularly denote a fluidic device as described herein which allows to convey fluid through microchannels having a dimension in the order of magnitude of less than 500 μm, particularly less than 200 μm, more particularly less than 100 μm or less than 50 μm or less. The sample separation apparatus may also be configured as a nanofluidic device. The term "nanofluidic device" may particularly denote a fluidic device as described herein which allows to convey fluid through nanochannels having even smaller dimensions than the microchannels.

BRIEF DESCRIPTION OF DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

Figure 1:
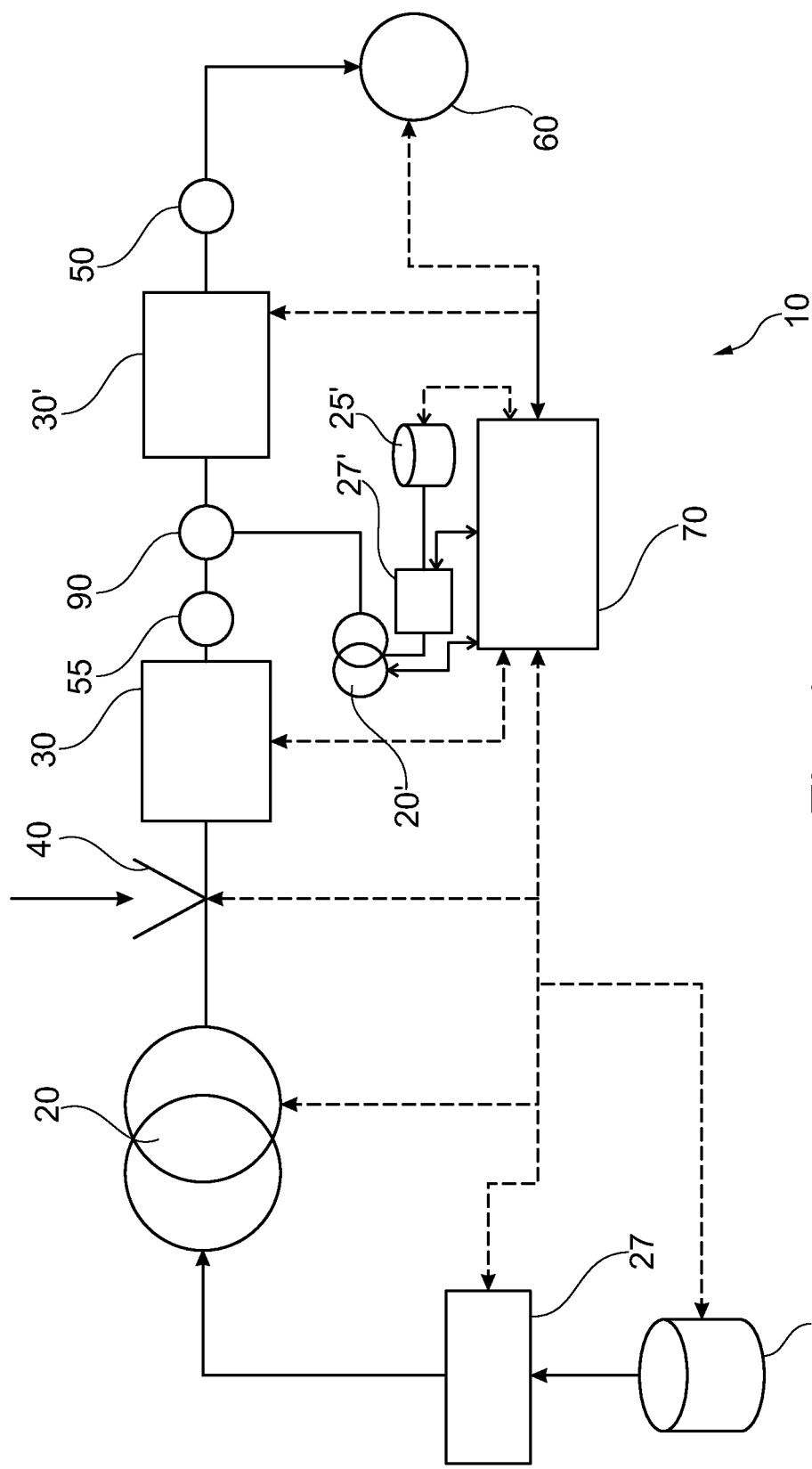
FIG. 1 illustrates a two-dimensional liquid chromatography system according to an exemplary embodiment.

The illustration in the drawing is schematically.

DETAILED DESCRIPTION

In an embodiment of a two-dimensional separation technique, a progress of a first dimension separation is accompanied by a successive or gradual adjustment of parameters along a second dimension. In the following, some basic cognitions of the present inventor will be mentioned based on which embodiments of the invention have been developed.

In an embodiment, a two-dimensional liquid chromatography (2D-LC) system is provided in which a second dimension gradient is adapted to an actual first dimension condition. In other words, a second dimension parameter may drift while the first dimension runs a gradient.

In two-dimensional chromatography systems usually the individual separations are optimized independently. In order to optimize for maximum peak capacity (pc), a preferred goal is to achieve orthogonal separations in both of the dimensions. Only then the theoretically achievable maximum pc value equals the product of both individual pc values in the first dimension $pc\text{-}1^{st}$ and in the second dimension $pc\text{-}2^{nd}$:

$$pc = pc\text{-}1^{st} * pc\text{-}2^{nd}$$

But very often this is not achieved in practice. Limitations in either the stationary phase available or the character of sample components commonly lead to the fact that some common component is found in both individual separations. In many examples one may notice that there is a substantial commonality. Peaks are assorted not randomly across the whole display space, but more arranged closely around a central line. In many cases, there is less chance for a peak elution early in first dimension and still being very late in second dimension. Likewise peaks eluting late in first dimension have low probability to elute early in second dimension. Consequently, with the very independent operation of the two individual separation dimensions one may lose tuning power.

Starting with the second dimension first, in order to fulfill the Nyquist sampling criteria it may be desired to run as fast as possible. So it is possible to employ very short analysis cycles: 1. In order to have decent stacking on the head of the second dimension column it may be desired to start low with the gradient. 2. In order to ensure that the second dimension column is cleaned before the next cycle, one may raise elution strength to the maximum. A natural result is that one will run the fast dimension in full span, for RP (reversed phase) separations usually 0%-100% organic at maximum speed.

According to an exemplary embodiment of the invention, a tune-type control of a sample separation system allows to combine the methods from both dimensions. In a situation that there is substantial non-orthogonality given, this dependent operation may gain peak capacity by the fact that empty spaces in the 2D plot can be used and filled with peaks. Basically it is possible for a user to zoom into the area where there are actually peaks of interest, spreading these given peaks across the field given. A gist is that the method for the second dimension may be set up in a way, which supports tune-type parameters. Instead of a list of parameters this special second method now contains controlled variables (in other sections of this application also discussed in terms of parameters and parameterization).

In the following, two cases are discussed:

Case 1): Such variable could be, as a simple example, the column temperature of the second dimension column. For instance, a user is doing RP×RP separations with different columns in both dimension. There is a certain chance that one column allows separation of substances, which are not separated on the other, and vice versa. In such a regime it is possible that along the first dimension time, the preselected substances modulated into the second dimension then elute preferentially pretty late in the second dimension gradient. If a user now programs the column temperature in the second dimension column to raise gradually from one to the other second dimension run, then it is possible to mobilize later sample groups to elute earlier. Some of them may still elute later, even at high temperatures. So it is advantageously possible to gain peak capacity.

Case 2): One could have a drifting gradient. Assuming a case in which a user is doing RP×RP separations with different columns in both dimension, but now the user commands a drift on the gradient settings. Because early in the first dimension time the modulated peak groups show less retention (otherwise they would not appear early), a user may not need to run all the way to 100% organic to clear the second dimension column. So a user will command the second dimension gradient sloping initially 0-60% organic, while with sequential second dimension runs you increase the top end of composition, gradually from 60% to 100%. up to a final stage with a gradient 0-100%.

This way it is possible to gain by a more flat gradient elution, separating low retentive peak groups better (filling for instance an upper left region of a display area), while at the same time still one can employ stronger elution towards the end of the first dimension run.

Likewise it is possible to gain by drifting the initial value of the second dimension gradient. While a user may start low in organic to achieve decent stacking for peaks showing low retention, eluting in a matrix of say 10% B, there is a good chance to achieve sufficient stacking still in later first dimension runtimes, where peaks elute in 50% B matrix. So a user may command the second dimension gradient sloping initially 0-100% organic, while with sequential second dimension runs a user may increase the low end of composition, gradually up to 40-100%. This way a user may gain by a more flat gradient elution, separating low retentive peak groups better, this time achieving faster second dimension elution (filling for instance a lower right region of a display area) more towards the end of the first dimension run.

Referring now in greater detail to the drawings, FIG. 1 depicts a general schematic of a liquid separation system 10. A first pump 20 receives a mobile phase (also denoted as fluid) from a first solvent supply 25, typically via a first degasser 27, which degases and thus reduces the amount of dissolved gases in the mobile phase. The first pump 20—as a mobile phase drive—drives the mobile phase through a first separating device 30 (such as a chromatographic column) comprising a stationary phase. A sampling unit 40 can be provided between the first pump 20 and the first separating device 30 in order to subject or add (often referred to as sample introduction) a sample fluid (also denoted as fluidic sample) into the mobile phase. The stationary phase of the first separating device 30 is configured for separating compounds of the sample liquid.

A second pump 20' receives another mobile phase (also denoted as fluid) from a second solvent supply 25', typically via a second degasser 27', which degases and thus reduces the amount of dissolved gases in the other mobile phase. By a fluidic valve 90, the first dimension (reference numerals 20, 30, . . . ) of the two-dimensional liquid chromatography system 10 of FIG. 1 may be fluidically coupled to the second dimension (reference numerals 20', 30', . . . ). The fluidic sample is separated into multiple fractions by the first dimension, and each fraction, or a part/slice of it, is modulated into the second separation path and further separated into multiple sub-fractions by the second dimension.

A detector 50 is provided for detecting separated compounds of the sample fluid. An optional further detector 55 is arranged upstream of the valve 90 and may be used for operating the device 10 in a heart-cutting operation. A fractionating unit 60 can be provided for outputting separated compounds of sample fluid.

While each of the mobile phases can be comprised of one solvent only, it may also be mixed from plural solvents. Such mixing might be a low pressure mixing and provided upstream of the pumps 20, 20', so that the respective pump 20, 20' already receives and pumps the mixed solvents as the mobile phase. Alternatively, the pump 20, 20' might be comprised of plural individual pumping units, with plural of the pumping units each receiving and pumping a different solvent or mixture, so that the mixing of the mobile phase (as received by the respective separating device 30, 30') occurs at high pressure and downstream of the pump 20, 20' (or as part thereof). The composition (mixture) of the mobile phase may be kept constant over time, the so called isocratic mode, or varied over time, the so called gradient mode.

A data processing unit 70, which can be a conventional PC or workstation, might be coupled (as indicated by the dotted arrows) to one or more of the devices in the liquid separation system 10 in order to receive information and/or control operation. For example, the data processing unit 70 might control operation of the pump 20, 20' (e.g. setting control parameters) and receive therefrom information regarding the actual working conditions (such as output pressure, flow rate, etc. at an outlet of the pump). The data processing unit 70 might also control operation of the solvent supply 25, 25' (e.g. setting the solvent/s or solvent mixture to be supplied) and/or the degasser 27, 27' (e.g. setting control parameters such as vacuum level) and might receive therefrom information regarding the actual working conditions (such as solvent composition supplied over time, flow rate, vacuum level, etc.). The data processing unit 70 might further control operation of the sampling unit 40 (e.g. controlling sample injection or synchronization sample injection with operating conditions of the pump 20). The respective separating device 30, 30' might also be controlled by the data processing unit 70 (e.g. selecting a specific flow path or column, setting operation temperature, etc.), and send—in return—information (e.g. operating conditions) to the data processing unit 70. Accordingly, the detector 50 might be controlled by the data processing unit 70 (e.g. with respect to spectral or wavelength settings, setting time constants, start/stop data acquisition), and send information (e.g. about the detected sample compounds) to the data processing unit 70. The data processing unit 70 might also control operation of the fractionating unit 60 (e.g. in conjunction with data received from the detector 50) and provides data back. The data processing unit 70 may include a storage device 75, which allows to store all or selected information of the analytical process and also to retrieve stored information (which may be advantageous for the above-mentioned scouting operation) from previous analytical processes.

In the following, referring to FIG. 2, a two-dimensional liquid chromatography separation system 200 according to an exemplary embodiment of the invention will be explained in more detail.

Before describing the operation or control modes according to an embodiment of the invention, the structure of the two-dimensional liquid chromatography apparatus 200 will be described. A control unit 202 is provided which can be a processor (such as a microprocessor or a central processing unit, CPU) or a set of processors and which is configured for controlling entire operation of the two-dimensional liquid chromatography apparatus 200. In a hierarchical approach some or all of the individual functions may have their own processor, so that processors may then communicate to perform a concerted function (for instance to enable a second dimension pump to obtain information regarding the progress of the first dimension). As will be described below in more detail, the control unit 202 centrally controls all other components of the two-dimensional liquid chromatography apparatus 200. This is indicated schematically in FIG. 2 by dotted lines.

Figure 2:
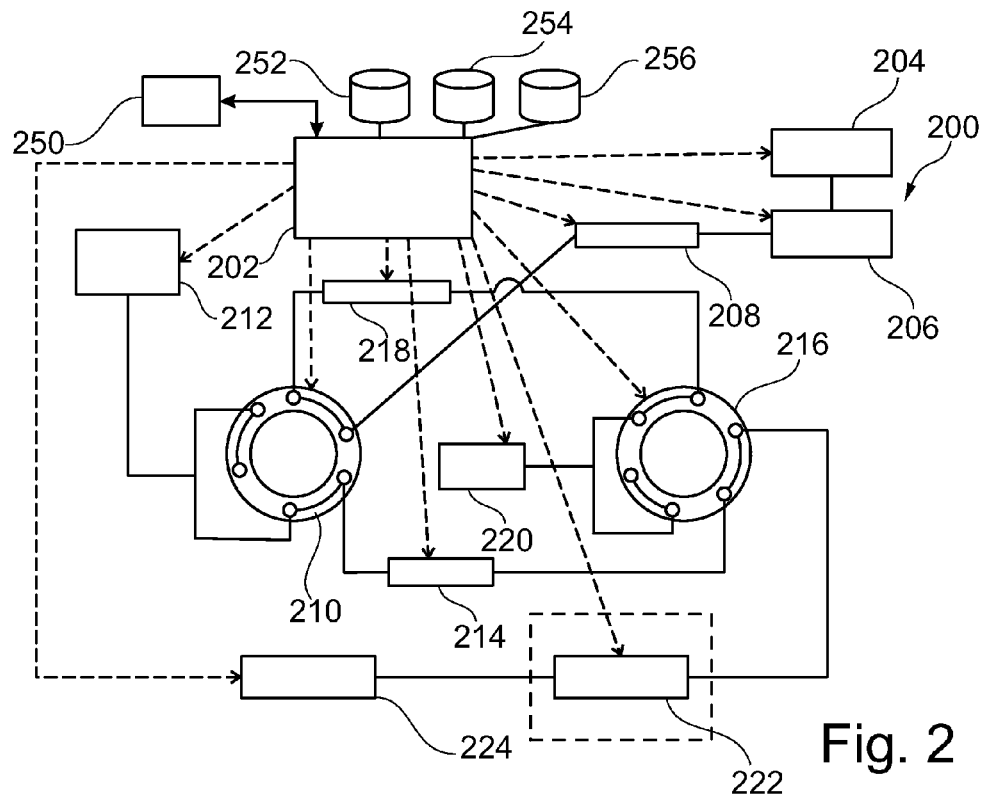
FIG. 2 illustrates a sample separation apparatus for two-dimensional liquid chromatography having a control device according to an exemplary embodiment of the invention.

A first dimension pump 204 is provided which is capable of pumping a desired solvent composition for a liquid chromatography separation through the various fluidic members shown in FIG. 2. In an autosampler 206, a fluidic sample to be separated may be injected into the mobile phase provided by the first dimension pump 204. A first dimension separation column 208 is arranged downstream of the autosampler 206. The first dimension separation column 208 corresponds to the first separation unit 30 shown in FIG. 1. A gradient run, or any other operation mode such as an isocratic mode, can be applied to separate the fluidic sample into different fractions which will then be subjected to further separation downstream of the first dimension column 208. From here, the separated fractions can be conducted into a first fluidic valve 210 having different fluidic ports shown as dots in FIG. 2. Furthermore, a number of arcuate grooves are shown at the first fluidic valve 210 in FIG. 2 interconnecting fluidically with specific ones of the ports, depending on the switching state of the first fluidic valve 210. The first fluidic valve 210 is formed of two valve members, a rotor and a stator, one of which having the ports and the other having the grooves. Alternatively it can be formed with two rotors, each having an independent motion drive. Alternatively the valve function can be achieved by a combination of connected on/off valves. In an operation mode shown in FIG. 2, the separated fluidic sample fraction downstream the first dimension column 208 is subsequently guided through the first fluidic valve 210 into a first loop 218 (which may for instance have a volume of 20 μl). When passing the loop 218, the separated fluidic sample pushes the loop's content through a second fluidic valve 216 which is constituted similar to the first fluidic valve 210. From here, the original content of the first loop 218 can be guided into a waste container 220. For comprehensive 2D-LC operation it is desired not to lose any original sample substance to waste. This way quantification of sample compounds is allowed to be correct.

However, upon correspondingly switching the valves 210, 216, the fluidic sample, after being separated by the first separation column 208 into a plurality of fractions, can be guided through a second loop 214 (having for instance an internal volume of 20 μl) while at the same time the second dimension pump 212 drives the actual content (slice of a previous fraction) of first loop 218 from there through the second fluidic valve 216 into a second dimension separation column 222. In the shown embodiment, as indicated by the dotted box, the second dimension column 222 may be arranged in an oven so as to be heated to a temperature of for instance 70° C. during the second dimension separation. While passing the second dimension column 222, each fraction of the fluidic sample which has already been separated by the first dimension column 208 may be further separated into a plurality of sub-fractions which can then be passed to a detector 224 to be detected and/or quantified individually.

In the following, control of the sample separation apparatus 200 will be explained in further detail.

The apparatus 200 comprises a user interface 250 bidirectionally coupled to the control unit 202 and adapted for allowing a user to select a certain chromatographic method to be executed and for displaying the method or operation mode as well as measurement results visually on a display (such as a liquid crystal display, a cathode ray tube, a plasma display or the like). Such a user interface 250 may include an input unit such as a touch-sensitive screen, a joystick, a keypad, a button, etc., allowing a user to input commands, parameters, data and instructions to the control unit 202. With such a user interface 250, a user may design, store and document a way of operating apparatus 200 in a convenient manner.

The sample separation system 200 is configured so that the primary separation sequence executed on the first dimension column 208 and the secondary separation sequences executed on the second dimension column 222 form part of a closed, common single chromatographic method defined by a closed, single common specification (or description) of the sample separation involving a set of parameters. In other words, the architecture of the applied chromatographic method is such that the first and the second dimension separation is integral and not splittable. Hence, during the entire separation procedure or during the measurement time interval, it can be prevented that the separation method needs to be changed by a user during execution of the sample separation or during the measurement time interval, which would be cumbersome for a user.

This chromatography method, in terms of the second separation sequences, is characterized by a parameterized shape function (see for instance FIG. 12) defined uniformly for at least two or all secondary separation sequences, i.e. defining a general shape of a time dependence of the solvent composition as repeated multiple times for separating fractions into sub-fractions. One or multiple shape functions among which a user may make a choice may be stored in a shape function database 252 to which the control unit 202 has access. The shape function is parameterized which means that only its general shape is predetermined, whereas a number of parameters may be selected so as to individualize the shape function for each second separation sequence separately. These parameters may be described in terms of and derived from a development instruction defining the parameters of the shape function over a progress of the first separation sequence. Such a development instruction may be defined by means of a development function (see for instance FIG. 13) stored in a development function database 254 defining development of the parameters. It is also possible that such a development instruction is defined by means of concrete parameter values stored in a development database 256 (defining for each of the secondary sequences an individual parameter set individualizing or defining the respective secondary separation sequence). By this approach of enabling the control unit 202 to access pre-populated or user-defined databases 252, 254, 256 for adapting the secondary separation sequences over a progress of the primary separation sequence, adaptation of the second dimension of a 2D chromatographic system is rendered very user-friendly making it dispensable for a user to manually choose tens, hundreds or thousands of parameters.

Figure 3:
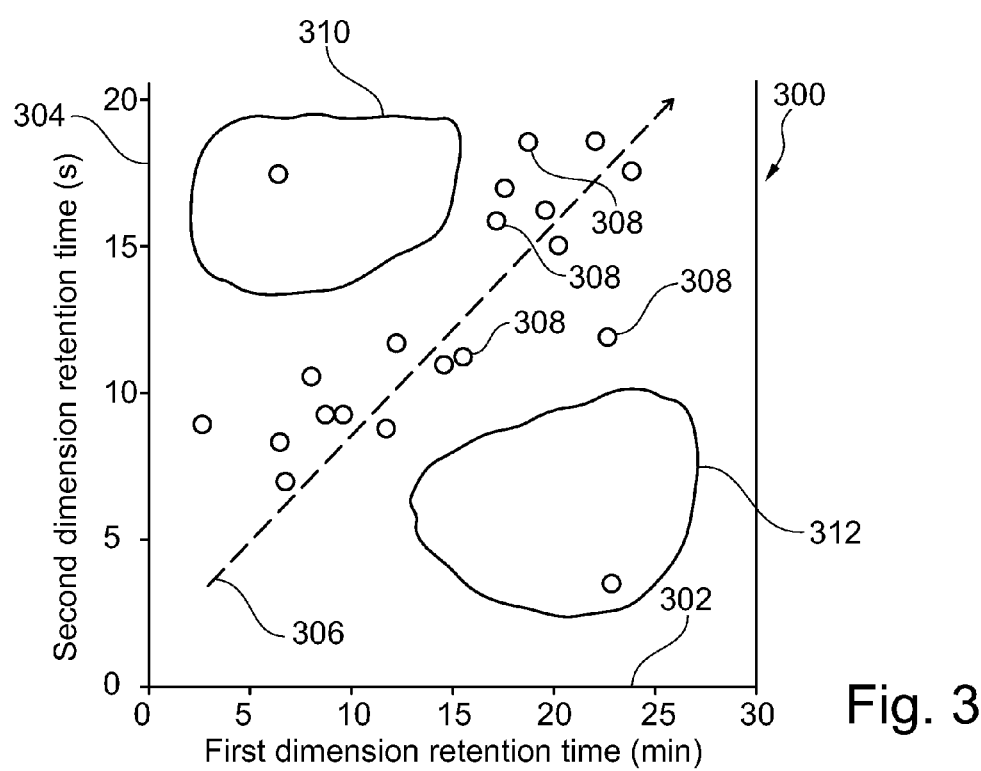
FIG. 3 shows a diagram indicating separated fractions and sub-fractions of a fluidic sample as obtained from two-dimensional liquid chromatography.

FIG. 3 now shows a two-dimensional chromatogram which can be obtained with an arrangement like the one shown in FIG. 2. Along an abscissa 302, a first retention time is plotted, i.e. indicating the separation performance of the first dimension column 208. Thus, the different fractions are arranged along the abscissa 302 in diagram 300. Along an ordinate 304 of the diagram 300, the sub-fractions each relating to a certain fraction, and as further separated by the second dimension column 222 are plotted.

As can be taken from FIG. 3, there is accumulation of corresponding peaks 308 (each of which relates to a certain sub-fraction) close to a symmetry axis 306, i.e. in a central portion of the two-dimensional plotting area of the diagram 300. In contrast to this, in regions 310 and 312, there are no or only few peaks visible. Consequently, the measurement time spent for regions 310 and 312 is not utilized efficiently. The reason behind this is that the two separation criteria applied by the first dimension column 208 and by the second dimension column 222 are different, but are not completely independent from one another. It is possible to say, both separation criteria share a common component or a vector. Based on this cognition, the control unit 302 may be configured in such a manner that the separation procedure particularly of the second dimension column 222 is adjusted so that the plotting area in FIG. 3 can be used more efficiently, i.e. that either the measurement time and therefore the resources required for measuring areas 310, 312 is utilized and/or that this measurement area is used for plotting interesting parts of the diagram 300 with better selectivity and/or higher accuracy, i.e. with a larger distance between different peaks and hence with a better resolution.

For this purpose, the control device 202 controls the first dimension column 208 to execute a primary separation sequence within a measurement time interval 420 (which corresponds to the about 30 minutes shown along the abscissa 302 in FIG. 3) for separating the fluidic sample into a plurality of fractions.

Figure 4:
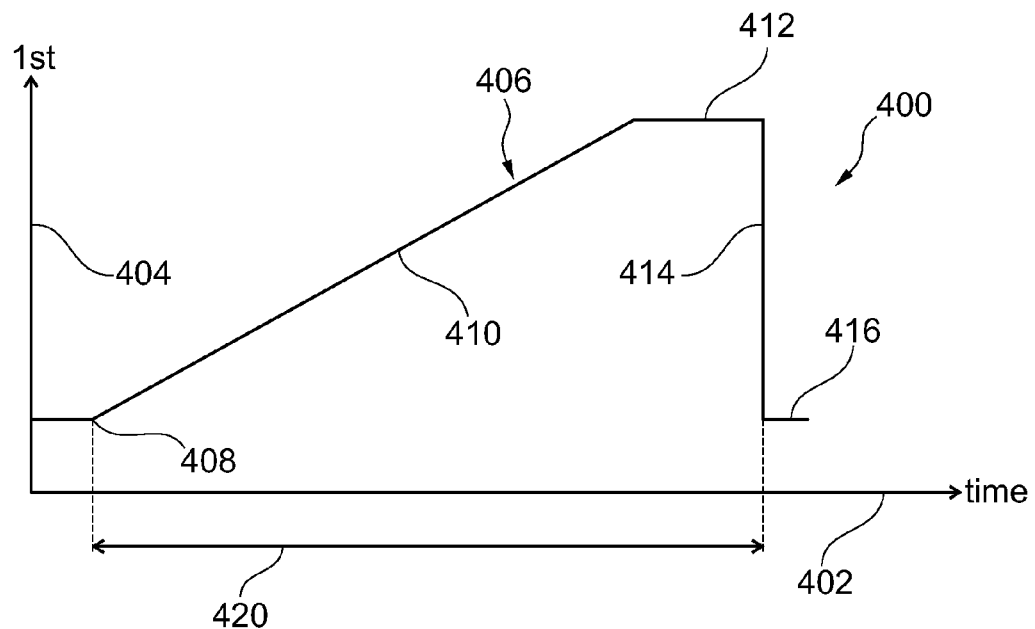
FIG. 4 shows a diagram indicating a primary separation sequence as performed by a first liquid chromatography column in a two-dimensional liquid chromatography apparatus as the one shown in FIG. 2.

A corresponding diagram 400 being indicative of the process flow of the primary separation sequence is shown in FIG. 4. Diagram 400 has an abscissa 402 along which the time is plotted. Along an ordinate 404, a solvent composition is plotted which indicates the time dependence of a solvent composition for a so-called chromatographic gradient run. Thus, starting from a base point 408, the solvent composition is continuously increased along a linear gradient curve 410 until a top point 412 is reached. Then the primary separation sequence is finished and goes back by an almost vertical line 414 to a base point 416, thereby reconditioning the separation column to be prepared for starting a new run.

Since the liquid chromatography apparatus 200 is configured for two-dimensional chromatography, the control device 202 also controls the operation of the second dimension column 222 in a more rapid way so that a plurality of secondary separation sequences is carried out during the measurement time spent for the primary separation sequence illustrated in FIG. 4. This is shown in more detail for instance in FIG. 5 which illustrates a diagram 500 indicating the various secondary separation sequences 504, 506, 508, . . . as executed on the second dimension column 222 under control of the control device 202. Along an abscissa 502, the time is plotted. Along an ordinate 404', the time dependence of the solvent composition during the multiple gradient runs executed as the secondary separation sequences is plotted as well. As can be taken from FIG. 5, during the measurement time of the primary separation sequence 400 shown in FIG. 4, multiple secondary separation sequences 504, 506, 508 are executed. By each of these secondary separation sequences 504, 506, 508 one of the fractions separated by the first dimension column 208, sliced by the modulator valve 90, is further separated into the plurality of the sub-fractions by second dimension column 222.

Figure 5:
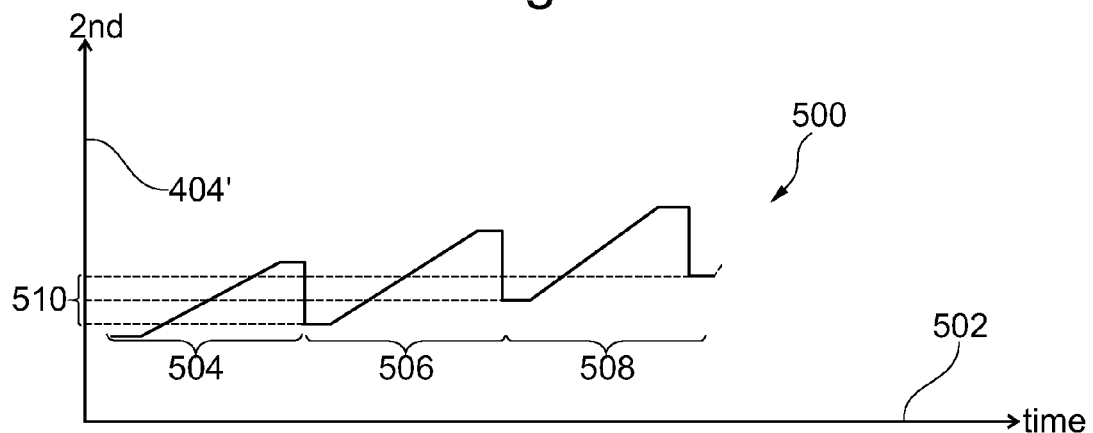
FIG. 5 shows a diagram illustrating a plurality of secondary separation sequences as carried out when operating a second chromatographic column during the liquid chromatography analysis relating to FIG. 4.

In the embodiment shown in FIG. 5, the base points of the various gradient runs 504, 506, 508, . . . continuously increase, as indicated by reference numeral 510.

Coming back to FIG. 3 and the measurement in areas 310, 312, such measurement regions can be avoided by allowing the control device 202, in a self-acting manner or under control of a user, to modify the parameters according to which the various secondary separation sequences (504, 506, 508 in FIG. 5) operate. Although not shown with reference numerals in FIG. 5, also these gradient runs can be identified by parameters such as the ones shown for the primary separation sequence of FIG. 4 with reference numerals 408, 410, 412, 414, 416.

Figure 6:
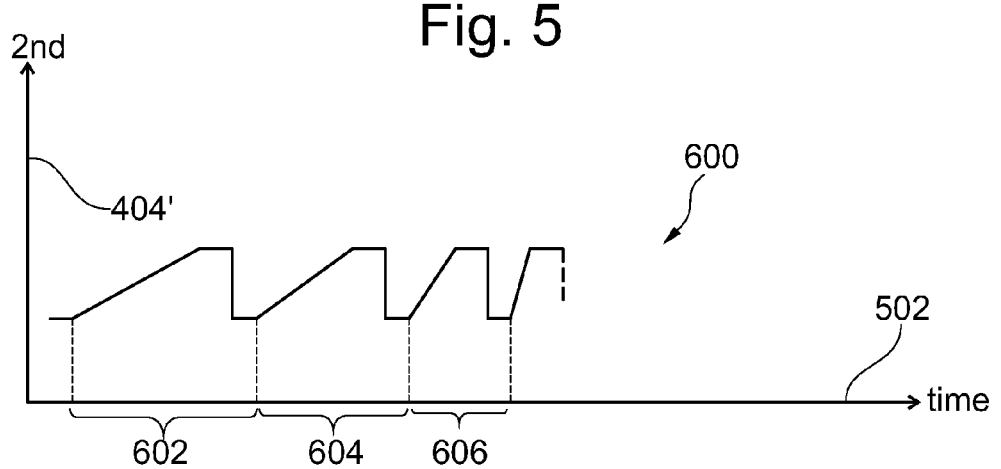
FIG. 6 shows another diagram showing alternative operation of the second separation column with other parameters than in FIG. 5.

FIG. 6 shows an alternative diagram 600 which is similar to diagram 500 with the exception that the various secondary separation sequences 602, 604, 606, . . . are now manipulated with regard to their parameters of the respective extensions along the abscissa 502. This will have another impact on the distribution of the peaks in diagram 300.

Figure 7:
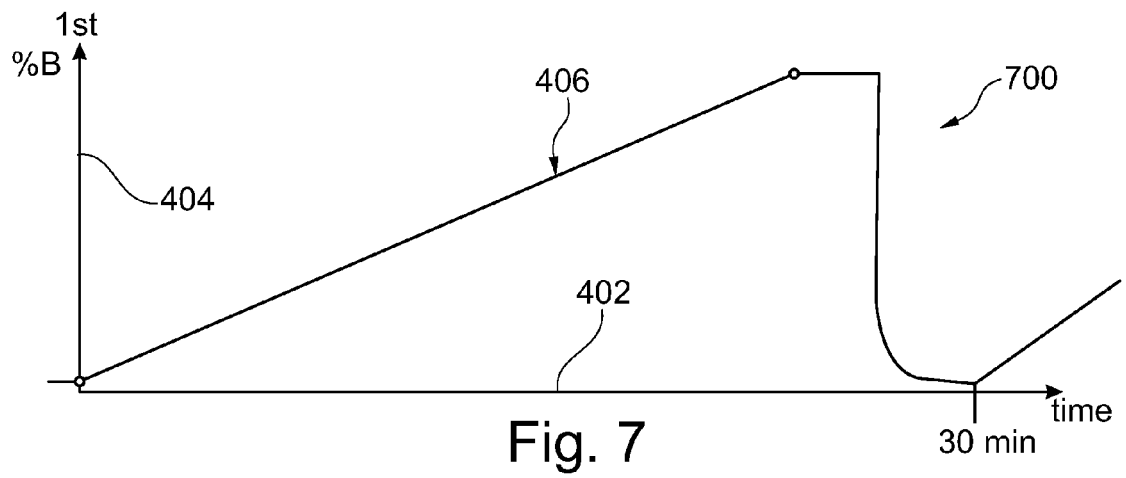
FIG. 7 shows another example of a primary separation sequence as performed by an upstream chromatographic column of a two-dimensional liquid chromatography apparatus.
Figure 8:
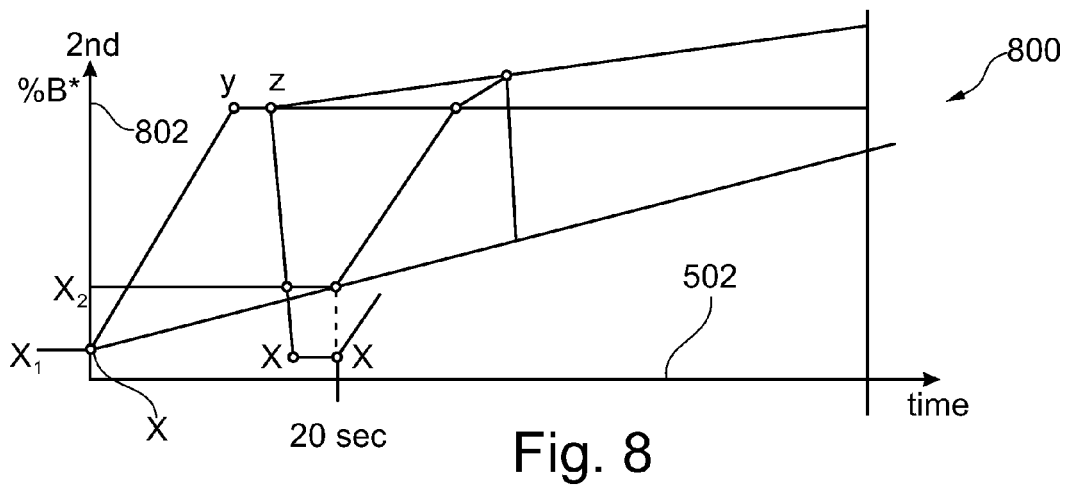
FIG. 8 shows a corresponding sequence of secondary separation sequences relating to the primary separation sequence of FIG. 7 and showing various parameters being modifiable so as to adjust the secondary separation sequences over the progress of the primary separation sequence according to FIG. 7.

FIG. 7 shows a diagram 700 indicating another primary separation sequence but being very similar to FIG. 4. In correspondence with this primary separation sequence, the various parameters which can be modified in the corresponding secondary separation sequences are shown in a diagram 800 of FIG. 8 having an ordinate 802. Particularly, the indicated parameters x, y, z can be adjusted for each of the secondary separation sequences individually.

Figure 9:
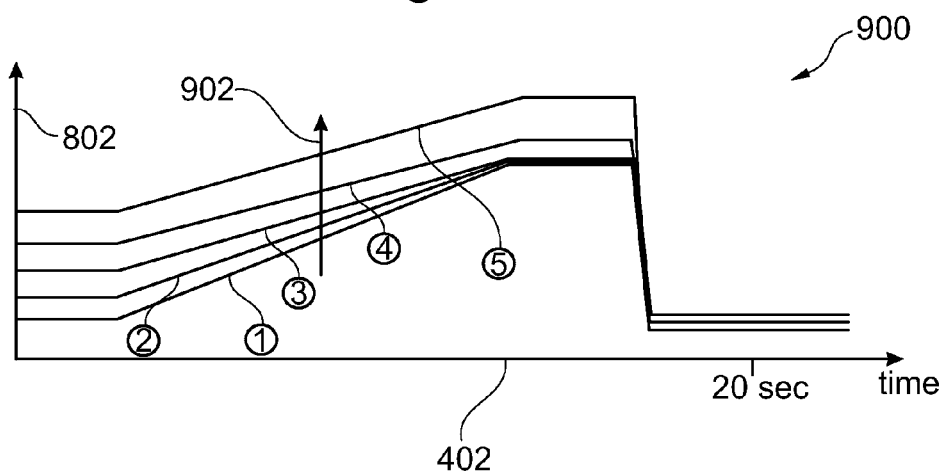
FIG. 9 shows multiple secondary separation sequences superposed to indicate as to how a parameter can be continuously altered over the various secondary separation sequences.

FIG. 9 shows the story in a different viewing angle. The abscissa now is the second dimension time, with sequential cycles overlaid. The arrow 902 indicates the progress of the first dimension separation. Here is depicted an advantageous embodiment in which the base points of the various gradient runs of the secondary separation sequences are continuously increased over the progress of the measurement time interval and of the primary separation sequence. This is indicated schematically by an arrow 902 showing the development of the parameters of the sequential secondary separation sequences (1), (2), (3), (4), and (5).

Figure 10:
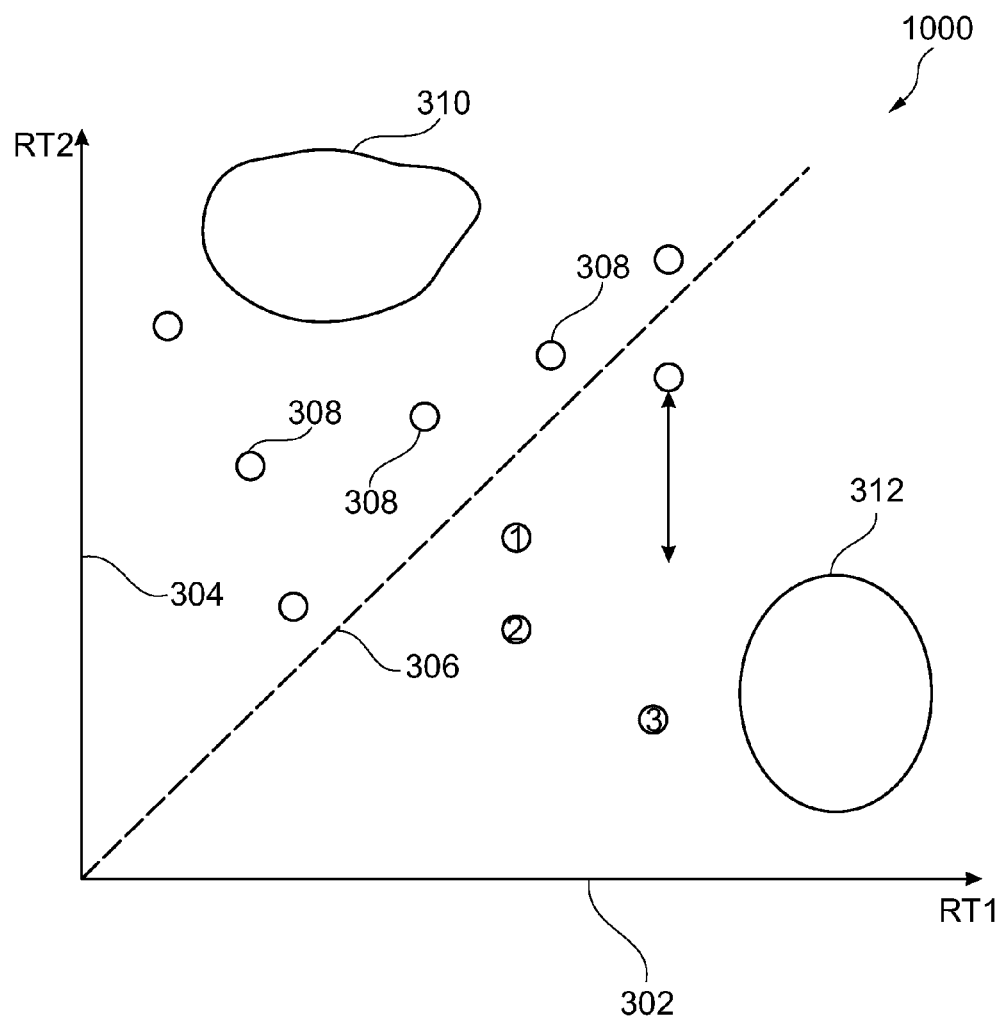
FIG. 10 shows a diagram similar to the diagram of FIG. 3 in which the influence of the modification of the parameters of the secondary separation sequence on the position of peaks and the management of the available display area is plotted.

An impact of an appropriate parameterization and parameter selection for secondary separation sequences along a progress of a primary separation sequence can be derived from FIG. 10. As indicated by a double arrow here, individual peaks 308 may be shifted upon correspondingly varying the parameters of the secondary separation sequence.

Figure 11:
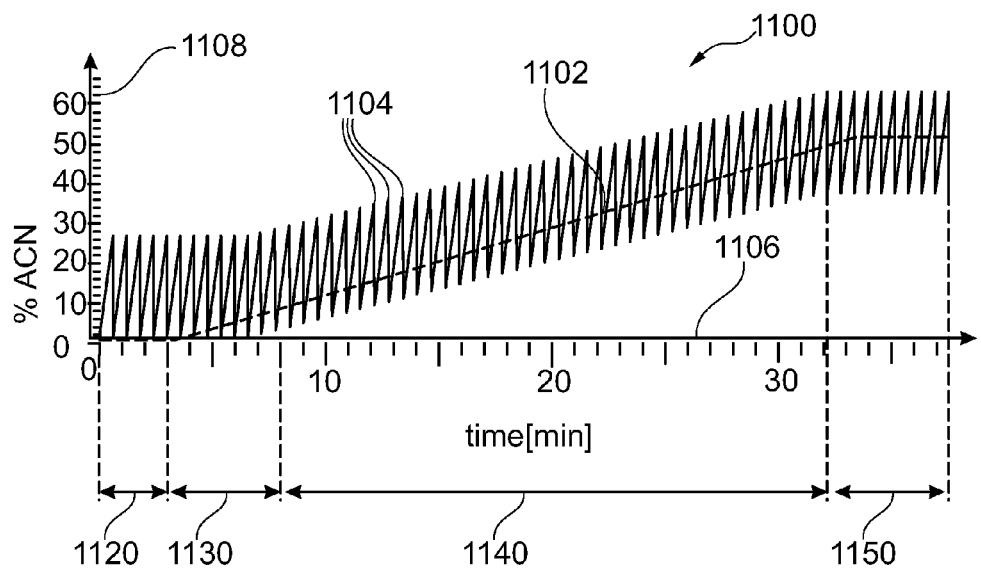
FIG. 11 shows a diagram plotting a primary separation sequence and multiple assigned secondary separation sequences of a common two-dimensional chromatographic method according to an exemplary embodiment of the invention.

FIG. 11 shows a diagram 1100 overlaying a primary separation sequence 1102 and multiple secondary separation sequences 1104 according to an exemplary embodiment of the invention. Along an abscissa 1106, a time is plotted. Along an ordinate 1108 of the diagram 1100, a solvent composition (ACN) is plotted. A first time section 1120, a second time section 1130, a third time section 1140, and a fourth time section 1150 are distinguished. A parameter defining a base point or start point for the gradient runs of the secondary separation sequences 1104 is continuously increased along a progress of the primary separation sequence 1102.

Figure 12:
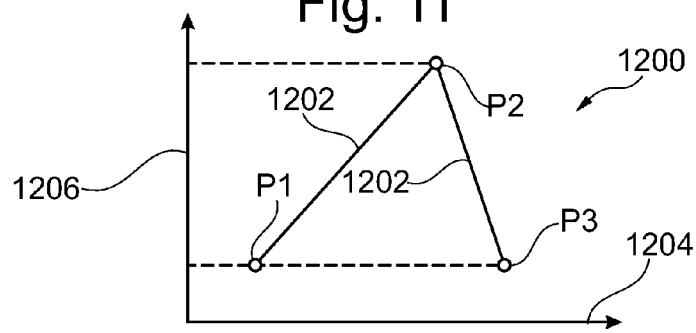
FIG. 12 shows a diagram illustrating a shape function for the multiple secondary separation sequences according to FIG. 11.

FIG. 12 shows a diagram 1200 illustrating a shape function 1202 for the multiple secondary separation sequences 1102 according to FIG. 11. Along an abscissa 1204, a time is plotted. Along an ordinate 1206 of the diagram 1200, a solvent composition (ACN) is plotted. The parameterized shape function 1202 is defined by parameters P1, P2, P3.

Figure 13:
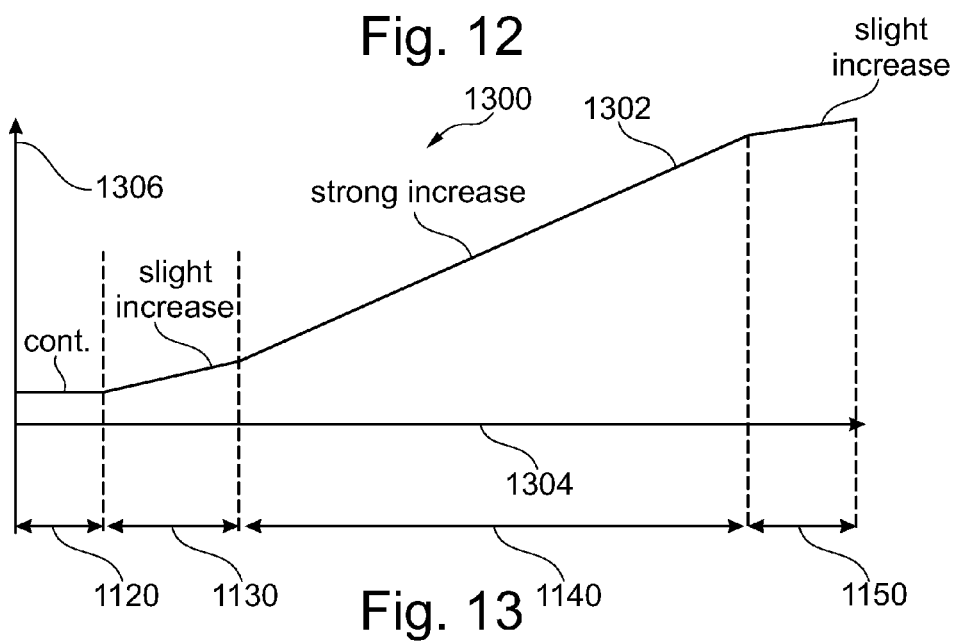
FIG. 13 shows a diagram illustrating a development function defining development of the parameters of the shape function for the multiple secondary separation sequences according to FIG. 11 and FIG. 12.

FIG. 13 shows a diagram 1300 illustrating a development function 1302 defining development of parameters P1 to P3 of the shape function 1202 for the multiple secondary separation sequences 1104 according to FIG. 11 and FIG. 12. For each of the sections 1120, 1130, 1140, 1150, the respective development of the parameters P1 to P3 is plotted. Parameters P1 to P3 remain constant in section 1120, slightly increase in section 1130, strongly increase in section 1140, and again slightly increase in section 1150. Alternatively, it is also possible that individual shape functions describe development of parameters P1 to P3 individually, both in terms of their magnitude and in terms of the timing relation (as shown e.g. FIG. 5 and FIG. 6).

It should be noted that the progression of the multiple secondary separation sequences along the first dimension separation time may be defined also by complex mathematical terms or functions, e.g. shape could be given as a series of Bezier functions and the progressive development of their parameters could be defined by a trigonomical function.

Alternatively the control unit 202 may use the results from a previous analytical run to construct an optimal pattern of sequential secondary separation sequences with the target to utilize the separation space more effectively.

It should be noted that the term "comprising" does not exclude other elements or features and the "a" or "an" does not exclude a plurality. Also elements described in association with different embodiments may be combined. It should also be noted that reference signs in the claims shall not be construed as limiting the scope of the claims.

The invention claimed is:

1. A control device for a sample separation apparatus for separating a fluidic sample, the sample separation apparatus comprising:
a first separation unit supplyable with the fluidic sample to be separated and a second separation unit downstream of the first separation unit and supplyable with the fluidic sample after treatment by the first separation unit, wherein the control device is configured for:
controlling the first separation unit to execute a primary separation sequence within a measurement time interval for separating the fluidic sample into a plurality of fractions;
controlling the second separation unit to execute a plurality of secondary separation sequences within the measurement time interval for further separating at least a part of the separated plurality of fractions into a plurality of sub-fractions, wherein the secondary separation sequences form part of a common sample separation method defined by a common specification of the sample separation involving a set of parameters; and
adjusting, over a progress of the primary separation sequence, at least one parameter according to which at least one of the plurality of secondary separation sequences is executed.

2. The control device according to claim 1, wherein the common specification of the common sample separation method comprises:
a parameterized shape relation defined uniformly for at least two of the secondary separation sequences; and
a development instruction defining the parameters of the shape relation for the at least two of the secondary separation sequences over a progress of the first separation sequence.

3. The control device according to claim 2, wherein the development instruction comprises one of the group consisting of:
a development relation defining development the parameters; and progressive parameter values for the parameters stored in a development database; and a sample specific shape and progression calculated based on data from a previous analytical separation.

4. The control device according to claim 1, wherein the primary separation sequence forms part of the same common sample separation method as the secondary separation sequences.

5. The control device according to claim 1, wherein the control device is configured for adjusting the at least one parameter so that gradient runs, as the plurality of secondary separation sequences, perform a drift while another gradient run is executed as the primary separation sequence.

6. The control device according to claim 1, wherein at least one of the primary separation sequence and the plurality of secondary separation sequences relates to a chromatographic gradient run.

7. The control device according to claim 1, wherein at least one of the plurality of secondary separation sequences is parameterized, wherein at least a part of corresponding parameters is adjusted over the progress of the primary separation sequence in accordance with a predefined progression rule.

8. The control device according to claim 1, wherein at least two of the plurality of secondary separation sequences relate to a parameterized shape relation defined as a gradient curve starting from a first local extreme value, subsequently rising or falling to a second local extreme value and then falling or rising to a next first local extreme value, wherein at least apart of corresponding parameters of the parameterized gradient curves is adjusted over the progress of the primary separation sequence.

9. The control device according to claim 8, wherein the control device is configured so that the first local extreme values are adjusted to continuously increase or to continuously decrease along a succession of the plurality of secondary separation sequences.

10. The control device according to claim 8, wherein the primary separation sequence relates to a parameterized shape relation defined as a gradient curve starting from a first local extreme value, subsequently rising or falling to a second local extreme value, and then falling or rising to the first local extreme value.

11. The control device according to claim 1, comprising a determining unit configured for determining a two-dimensional plot representing the separation of the fluidic sample into the plurality of fractions along a first dimension and for representing the separation of the separated plurality of fractions into the plurality of sub-fractions along a second dimension.

12. The control device according to claim 11, wherein the control device is configured for adjusting the at least one parameter so as to increase a degree of homogeneity according to which the sub-fractions are distributed over the two-dimensional area of the two-dimensional plot.

13. The control device according to claim 11, wherein the control device is configured for adjusting the at least one parameter so as to equally distribute the sub-fractions over the two-dimensional area of the two-dimensional plot.

14. The control device according to claim 11, wherein the control device is configured for determining information indicative of at least one local low-density region of peaks relating to the sub-fractions over the two-dimensional area of the two-dimensional plot, and is configured for adjusting the at least one parameter so that density of the peaks is increased in the at least one local low-density region of the two-dimensional plot as a result of the adjusting.

15. The control device according to claim 1, wherein the control device is configured for adjusting the at least one parameter in accordance with a user input.

16. The control device according to claim 1, comprising at least one of the following features:
the control device is configured for adjusting a solvent composition during a chromatographic run as the at least one parameter; the control device is configured for adjusting a time to volume characteristic during a chromatographic run as the at least one parameter; the control device is configured for adjusting a temperature of at least one of the group consisting of the first separation unit and the second separation unit as the at least one parameter.

17. A sample separation apparatus for separating a fluidic sample, the sample separation apparatus comprising
a first separation unit supplyable with the fluidic sample to be separated;
a second separation unit downstream of the first separation unit and supplyable with the fluidic sample after treatment by the first separation unit;
a control device according to claim 1 for controlling the first separation unit and the second separation unit.

18. The sample separation apparatus according to claim 17, comprising at least one of the following features:
the first separation unit and the second separation unit are configured so as to execute the respective sample separation in accordance with at least partially but not completely orthogonal separation criteria;
the first separation unit and the second separation unit are configured so as to execute the respective sample separation on identical separation media with at least one of the group consisting of different solvents, different steepness of elution gradients, different column temperatures, and different pressures, so that the separation criteria are partially but not completely orthogonal;
at least one of the first separation unit and the second separation unit is configured for performing a separation in accordance with one of the group consisting of liquid chromatography, supercritical-fluid chromatography, capillary electrochromatography, electrophoresis and gas chromatography;
the sample separation apparatus is configured as a two-dimensional liquid chromatography sample separation apparatus;
the sample separation apparatus is configured to analyze at least one physical, chemical and/or biological parameter of at least one compound of the fluidic sample;
the sample separation apparatus comprises at least one of the group consisting of a chromatography device, a liquid chromatography device, an HPLC device, a gas chromatography device, a capillary electrochromatography device, an electrophoresis device, a capillary electrophoresis device, a gel electrophoresis device, and a mass spectroscopy device;
the sample separation apparatus is configured to conduct the fluidic sample with a high pressure;
the sample separation apparatus is configured to conduct the fluidic sample with a pressure of at least 100 bar;
the sample separation apparatus is configured to conduct a liquid fluid;
the sample separation apparatus is configured as a microfluidic device;
the sample separation apparatus is configured as a nanofluidic device;
at least one of the group consisting of the first separation unit and the second separation unit is configured for retaining a part of components of the fluidic sample and for allowing other components of the fluidic sample to pass;
at least one of the group consisting of the first separation unit and the second separation unit comprises a separation column;
at least one of the group consisting of the first separation unit and the second separation unit comprises a chromatographic column;
at least a part of at least one of the group consisting of the first separation unit and the second separation unit is filled with a separating material;
at least a part of at least one of the group consisting of the first separation unit and the second separation unit is filled with a separating material, wherein the separating material comprises beads having a size in the range of 1 .mu.m to 50 .mu.m;
at least a part of at least one of the group consisting of the first separation unit and the second separation unit is filled with a separating material, wherein the separating material comprises beads having pores having a size in the range of 0.01 µm to 0.2 µm.

19. A process of separating a fluidic sample by a first separation unit supplyable with the fluidic sample to be separated and by a second separation unit downstream of the first separation unit and supplyable with the fluidic sample after treatment by the first separation unit, wherein the process comprises:
controlling the first separation unit to execute a primary separation sequence within a measurement time interval for separating the fluidic sample into a plurality of fractions;
controlling the second separation unit to execute a plurality of secondary separation sequences within the measurement time interval for further separating at least a part of the separated plurality of fractions into a plurality of sub-fractions, wherein the secondary separation sequences form part of a common sample separation method defined by a common specification of the sample separation involving a set of parameters;

adjusting, over a progress of the primary separation sequence, at least one parameter according to which at least one of the plurality of secondary separation sequences is executed.

20. A software program or product, stored on a data carrier, for executing a process according to claim 19, when run on a data processing system.

* * * * *